(12) United States Patent
Bergfjord et al.

(10) Patent No.: US 7,570,739 B2
(45) Date of Patent: Aug. 4, 2009

(54) RADIOTHERAPY APPARATUS AND PARTS THEREOF

(75) Inventors: Per Harald Bergfjord, Crawley (GB); Clifford William Perkins, Crawley (GB)

(73) Assignee: Elekta AB (publ), Stockholm (SE)

( * ) Notice: Subject to any disclaimer, the term of this patent is extended or adjusted under 35 U.S.C. 154(b) by 0 days.

(21) Appl. No.: 11/974,374

(22) Filed: Oct. 12, 2007

(65) Prior Publication Data

US 2009/0097614 A1     Apr. 16, 2009

(51) Int. Cl.
*A61N 5/10* (2006.01)
(52) U.S. Cl. .......................... 378/65; 378/193
(58) Field of Classification Search .................. 378/65, 378/68, 210, 193, 197
See application file for complete search history.

(56) References Cited

U.S. PATENT DOCUMENTS 3,656,407 A * 4/1972 Hause .......................... 91/490

\* cited by examiner

*Primary Examiner*—Jurie Yun
(74) *Attorney, Agent, or Firm*—Lahive & Cockfield, LLP; Anthony A. Laurentano

(57) ABSTRACT

A mount for a radiotherapy apparatus may include a cylindrical bearing surface to allow the mount to be supported in a rotateable manner, a housing extending from the bearing surface and having an extent in a direction along an axis of the cylindrical bearing surface, the mount having an axial through-hole which encompasses the axis of the cylindrical bearing surface, the housing having at least one opening communicating with the through-hole and extending in a direction transverse to the axis of the cylindrical bearing surface.

15 Claims, 9 Drawing Sheets

US 7,570,739 B2

RADIOTHERAPY APPARATUS AND PARTS THEREOF

FIELD OF THE INVENTION

The present invention relates to radiotherapy apparatus, and parts thereof including the supporting structures upon which the various active elements of the apparatus are mounted.

BACKGROUND ART

Radiotherapeutic apparatus is provided in a range of different morphologies to suit the particular type of treatment format that it is to provide. This includes gantry arrangements, in which a projecting arm carries a radiation source and is rotatable about an axis that is offset from the arm and coincident with the beam direction. It also includes arrangements in which a source is rotatable within a toroidal shell, into which a patient is placed.

SUMMARY OF THE INVENTION

This variety of arrangements reduces the flexibility of manufacturing processes and increases development costs. If certain elements of the apparatus could be made common to more than one arrangement then development costs could be shared, inventory could be reduced, and production processes could be made more flexible.

The present invention therefore provides a mount for a radiotherapy apparatus, comprising a cylindrical bearing surface to allow the mount to be supported in a rotatable manner, a housing extending from the bearing surface and having an extent in a direction along an axis of the cylindrical bearing surface, the mount having an axial through-hole which encompasses the axis of the cylinder, the housing having at least one opening communicating with the through-hole and extending in a direction transverse to the axis of the cylinder.

This mount can be used as the basis for a number of different radiotherapy systems. One such system comprises a support having a cylindrical bearing surface on which is mounted the cylindrical bearing surface of such a mount, an arm extending from a side of the mount in a direction in line with the axis of the cylindrical bearing surface, the arm comprising a linear accelerator adapted to emit a beam of therapeutic radiation from an end portion of the arm in a direction transverse to and towards the axis of the cylindrical bearing surface.

This system can further comprise one or more of a source of diagnostic radiation, a detector for diagnostic radiation and a detector for therapeutic radiation. These can be mounted on retractable arms, so as to be selectively retractable into the mount or extendable alongside the linear accelerator.

Typically, therapeutic radiation has an energy of at least 1 MeV and diagnostic radiation has an energy of at least 1 keV.

Another possible system comprises a support having a cylindrical bearing surface on which is mounted the cylindrical bearing surface of such a mount, a source of therapeutic radiation fixed to the mount and adapted to emit a beam transverse to and towards the axis of the cylindrical bearing surface though the at least one opening of the mount.

This system can also further comprise one or more of a source of diagnostic radiation, a detector for diagnostic radiation and a detector for therapeutic radiation.

It can further include a cover around the mount, the cover including a concave region extending into the axial through-hole of the mount.

BRIEF DESCRIPTION OF THE DRAWINGS

An embodiment of the present invention will now be described by way of example, with reference to the accompanying figures in which.

DETAILED DESCRIPTION OF THE EMBODIMENTS

Figure 1:
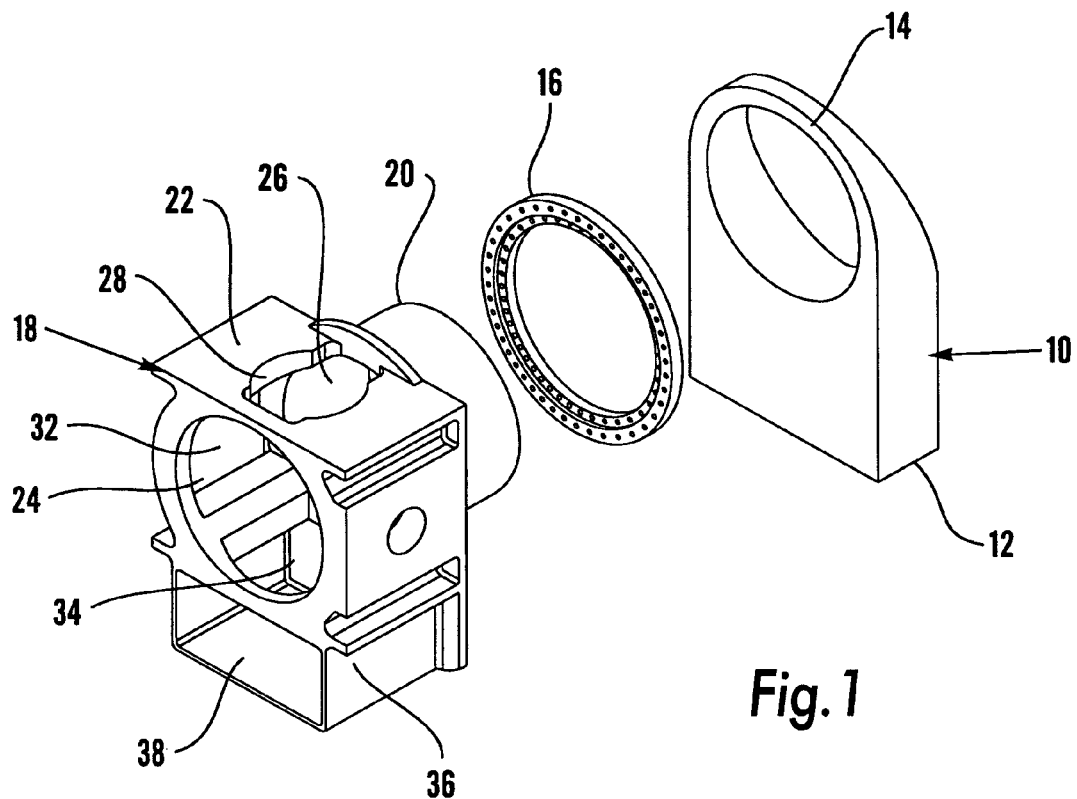
FIG. 1 shows a mount and support according to the present invention, dissembled.

FIG. 1 shows a stand 10 with a lower edge 12 that can be affixed to a floor or ground surface. The stand 10 rises generally vertically from its lower face 12, and has a horizontal through-hole whose internal face defines a generally annular ring section 14, disposed vertically above the lower base 12. A circular bearing 16 is fitted within the interior annular face of the ring 14, and supports a mount 18 by way of a corresponding cylindrical bearing surface 20 provided on the mount 18. The cylindrical bearing surface 20 comprises a tubular section whose exterior face provides the bearing surface, from one end of which is suspended the main body 22 of the mount 18. This main body 22 consists of a box section body with a circular aperture 24 at the front thereof and a circular aperture 26 at the rear thereof, with substantially flat top and side portions. The interior of the body 22 is generally open, thus allowing a clear passage through the interior of the mount 18 from the front aperture 24 to the rear aperture 26 and through the tubular section 20.

The top face has an aperture 28, for reasons which will be explained later. The same applies to the two side faces, which have a left aperture 30 and a right aperture 32. The bottom face includes an aperture 34 which leads into a box section 36 that is suspended beneath the body 22. The box section 36 is open at the top face to permit communication through the bottom aperture 34, and is likewise open at a front section 38.

Figure 2:
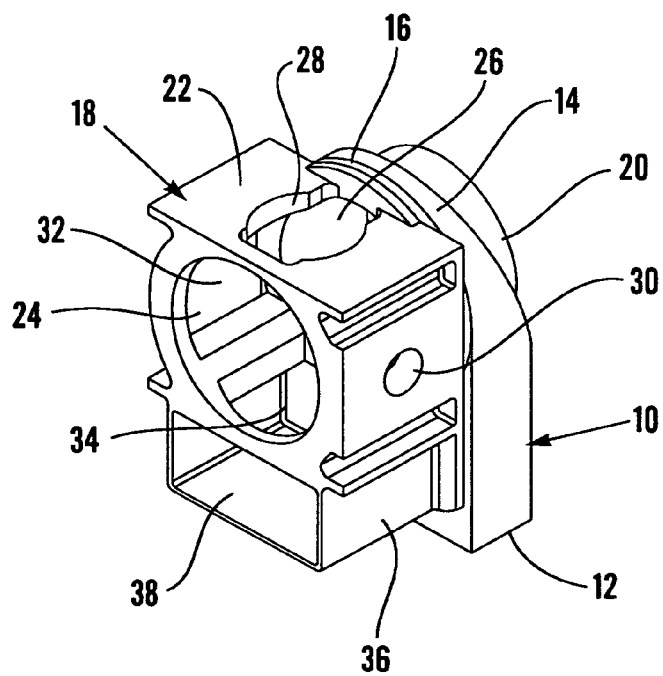
FIG. 2 shows the mount and support, assembled.
Figure 3:
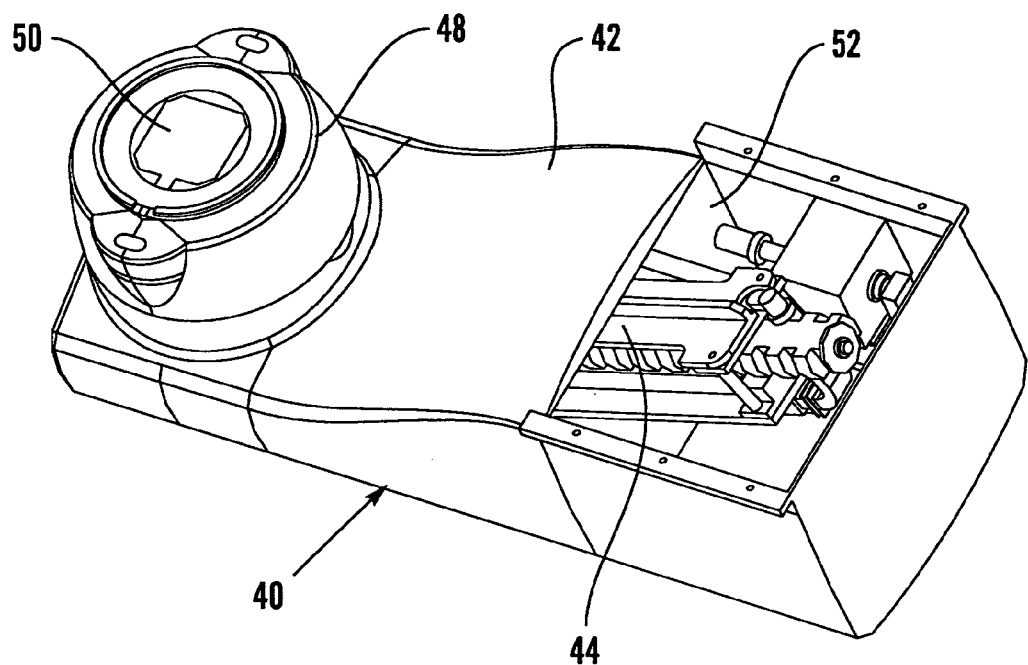
FIG. 3 shows a perspective view of a linear accelerator arm for use in the present invention.

FIG. 3 shows a linear accelerator arm 40 for use in conjunction with the mount shown in FIGS. 1 and 2. An exterior casing 42 covers a magnetron, accelerator 44 and associated elements which produce a high energy beam of electrons and deliver that beam to a beam-bending system 46 which conveys the beam to a radiation head 48 carrying the usual collimator set 50.

Figure 4:
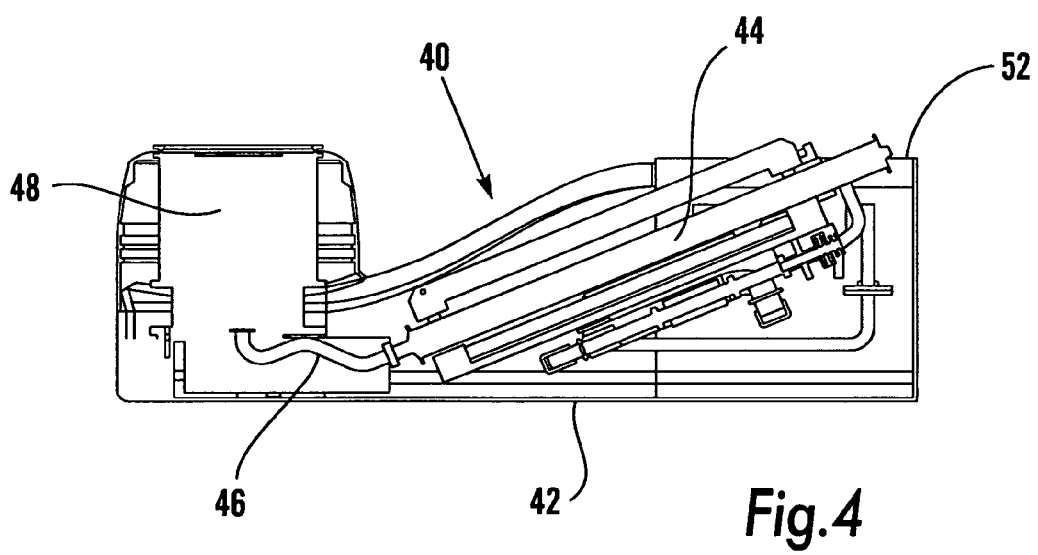
FIG. 4 shows a side sectional view of the linear accelerator arm.
Figure 5:
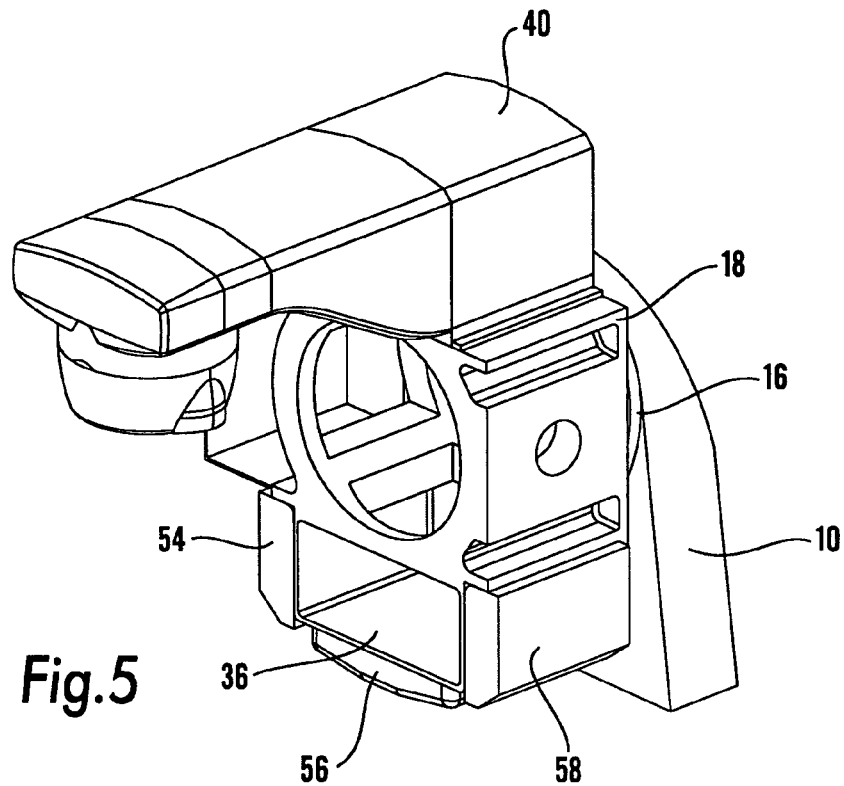
FIG. 5 shows a perspective view of the linear accelerator arm fitted to the mount.
Figure 6:
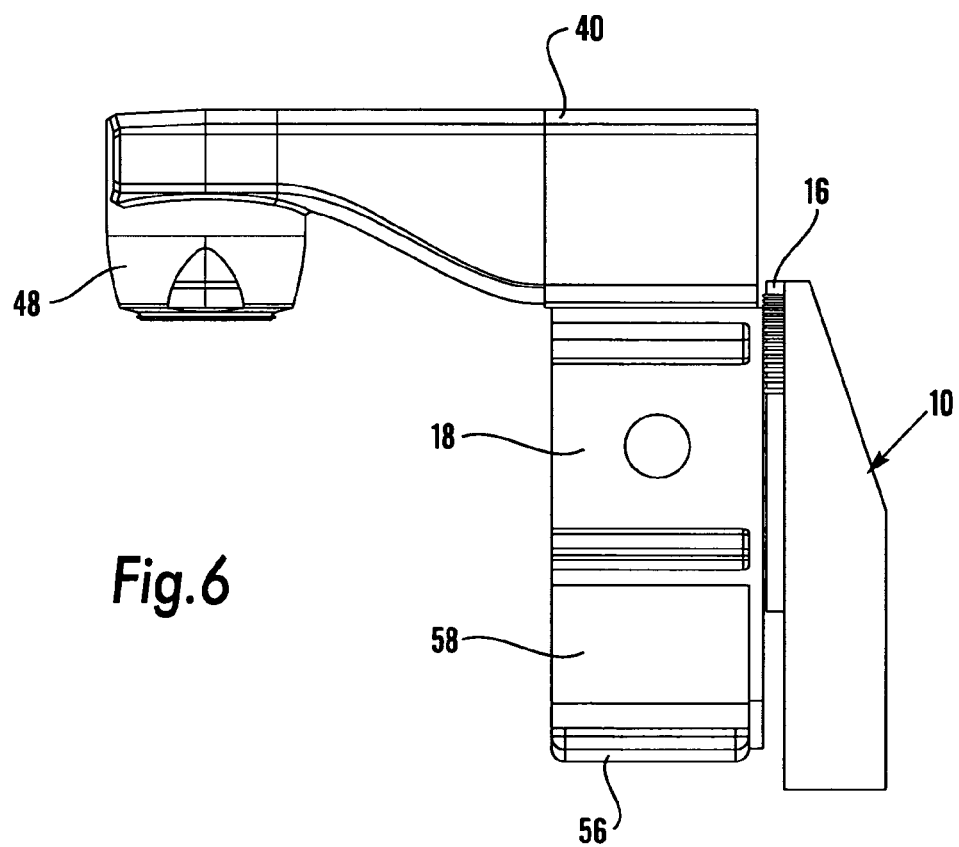
FIG. 6 shows a view from the side of the linear accelerator arm fitted to the mount.

This arm 40 can be fitted to the upper face of the mount body 22 as shown in FIGS. 5 and 6. An opening 52 (FIG. 4) in the linear accelerator casing 42 allows for connections to be made via the aperture 28 to both the linear accelerator 44 and to control lines for the upper parts of the arm 40. Counterweights 54, 56, 58 can be attached to the exterior of the box section 36 opposite the linear accelerator arm 40, so that the composite apparatus remains balanced around the cylindrical bearing surface.

The configuration shown in FIG. 3, with all necessary elements such as the waveguide and magnetron integrated into the arm to form a complete radiation generation module is, in this example, made possible by the use of a magnetron. As the magnetron is included in the module, the latter can be tested separately, i.e. after it has been manufactured and before it is attached to other parts of the modular system disclosed herein. This allows streamlining of the manufacturing process by revealing any remedial work that is required at an earlier stage of assembly.

Figure 7:
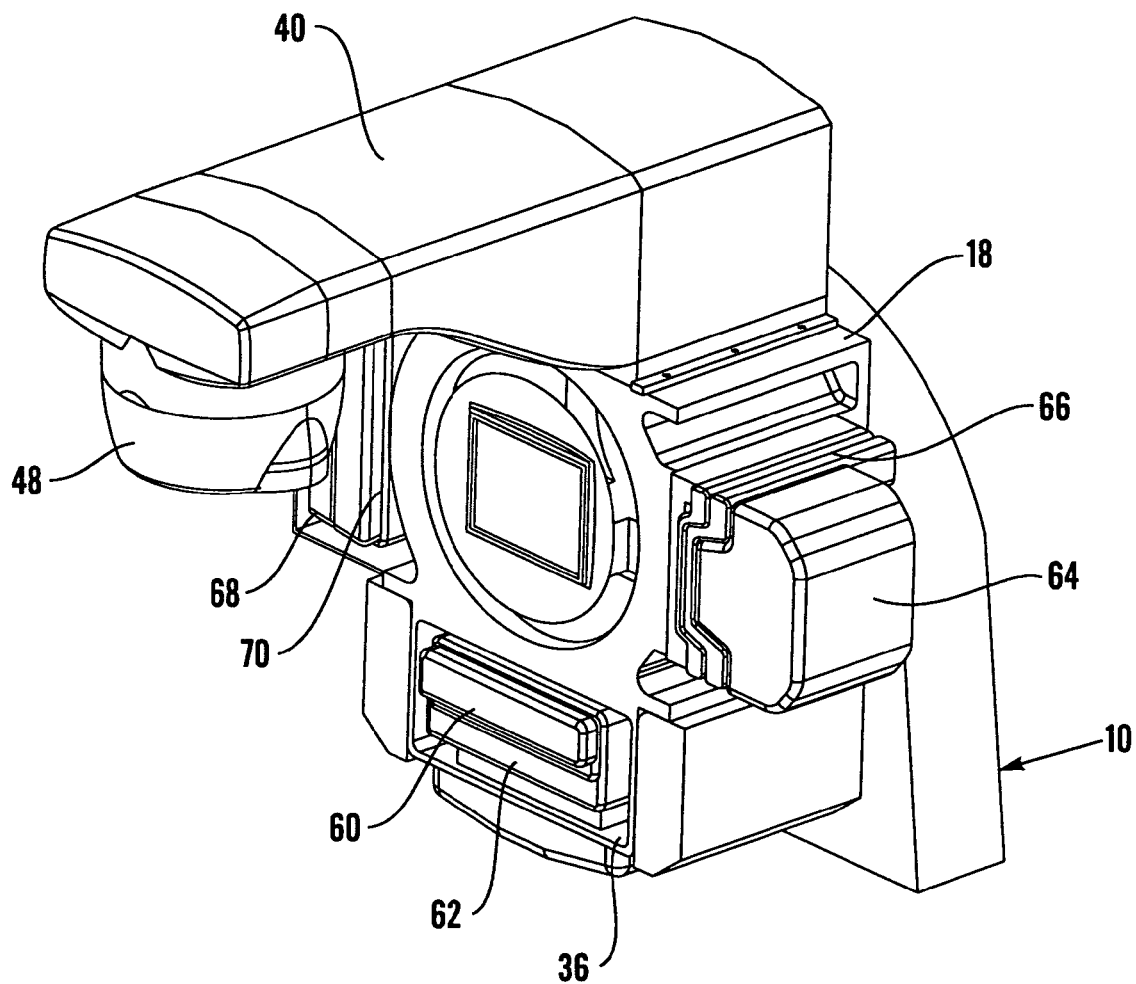
FIG. 7 shows a perspective view of the operative elements of linear-accelerator system based on the mount of the present invention.
Figure 8:
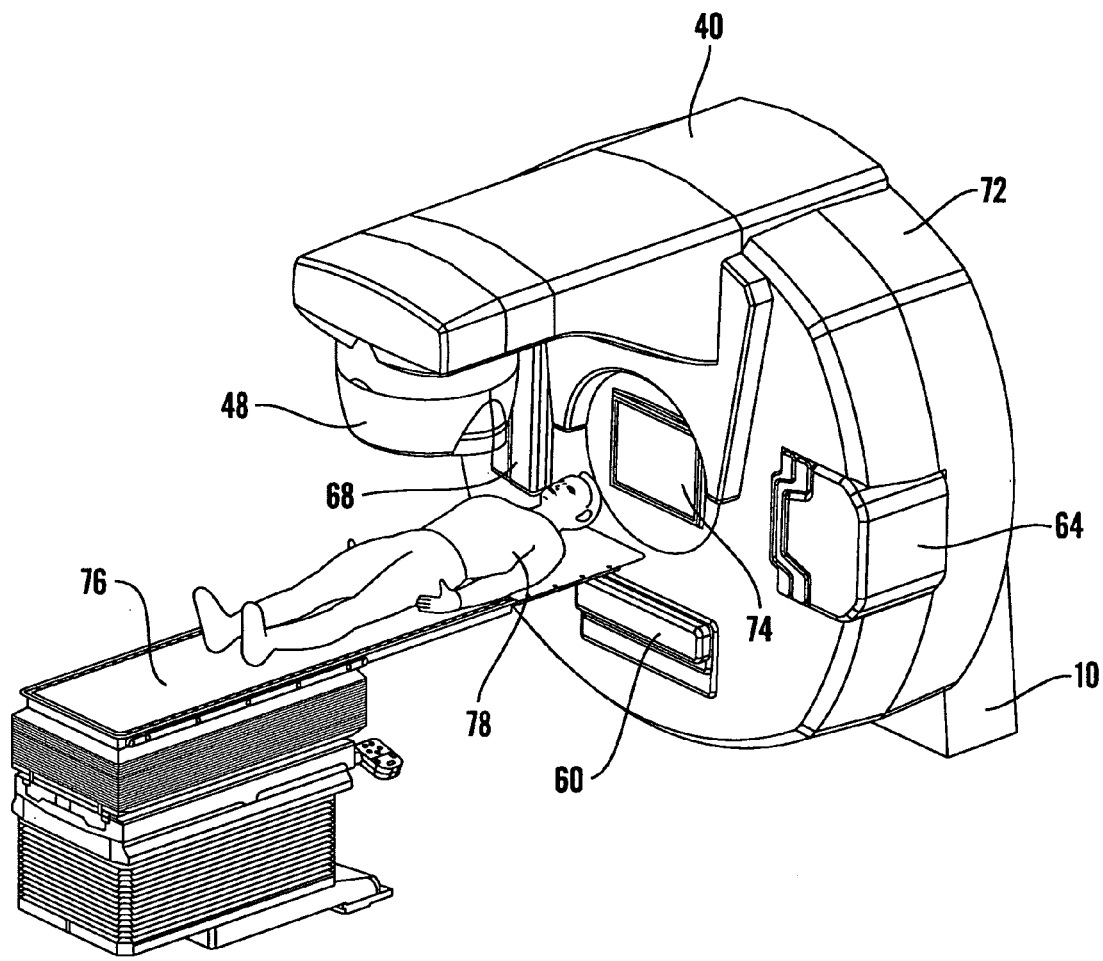
FIG. 8 shows the complete linear-accelerator system ready to treat a patient.

A flat panel detector 60 can then be fitted within the box section 36, as shown in FIG. 7. This is mounted on an extendable arm 62, so that the detector can be extended into position through the aperture 38 into a location opposite the radiation head 48. Likewise, a diagnostic x-ray tube 64 can be mounted on one lateral side of the mount 18 on a suitable extending arm 66, and a flat panel detector 68 for the diagnostic source 64 can be mounted on a similar extending arm 70 on the opposite lateral side of the mount 18. The entire apparatus can be enclosed in a suitable casing 72, as shown in FIG. 8. The central through-hole of the mount 18 can be employed to contain cable runs, conduits, controls and output devices for the apparatus, shown generically as 74 in FIG. 8.

Figure 9:
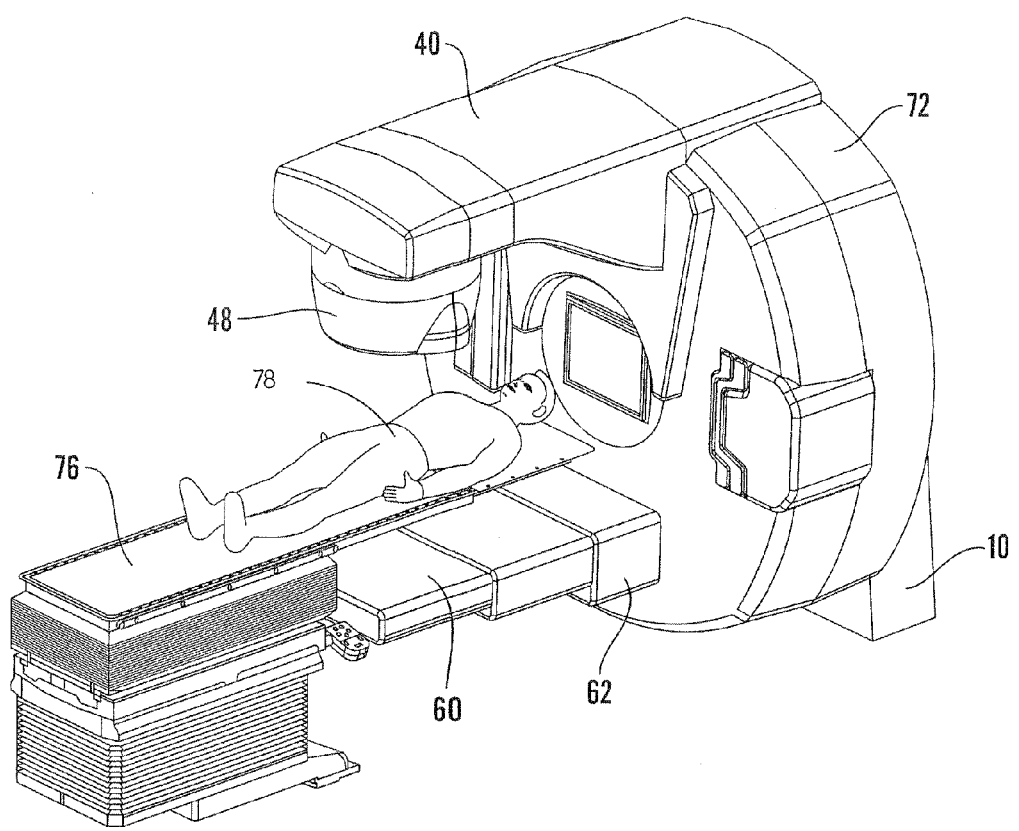
FIGS. 9 and 10 show the complete linear-accelerator system treating a patient.
Figure 10:
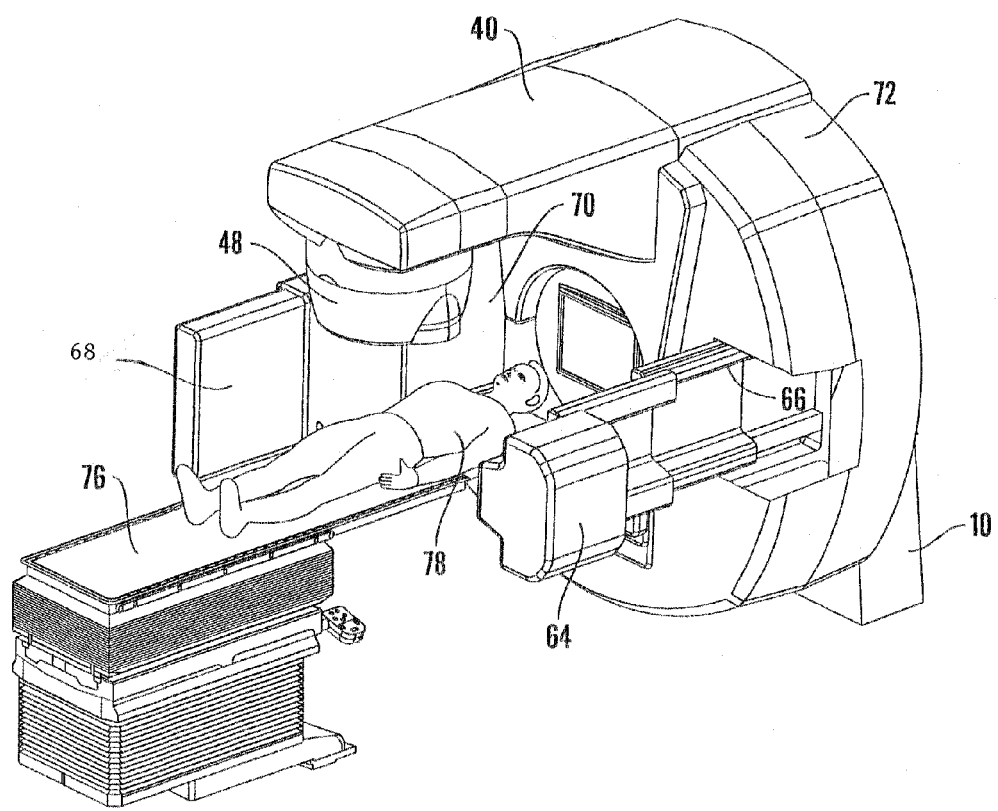

Together with the provision of a suitable patient table 76 this apparatus may be used to treat a patient 78. As and when required, the MV detector 60 can be extended on the extending arm 62 to acquire portal images, as shown in FIG. 9. FIG. 10 shows that as an alternative, or in addition, the diagnostic x-ray source 64 can be extended on its extendable arm 64 together with the diagnostic detector 78 on its extendable arm 70 so that as the apparatus rotates around the patient on the circular bearing 16, diagnostic images can be created. These can, if desired, be built up into a computed tomography scan (CT scan).

Figure 11:
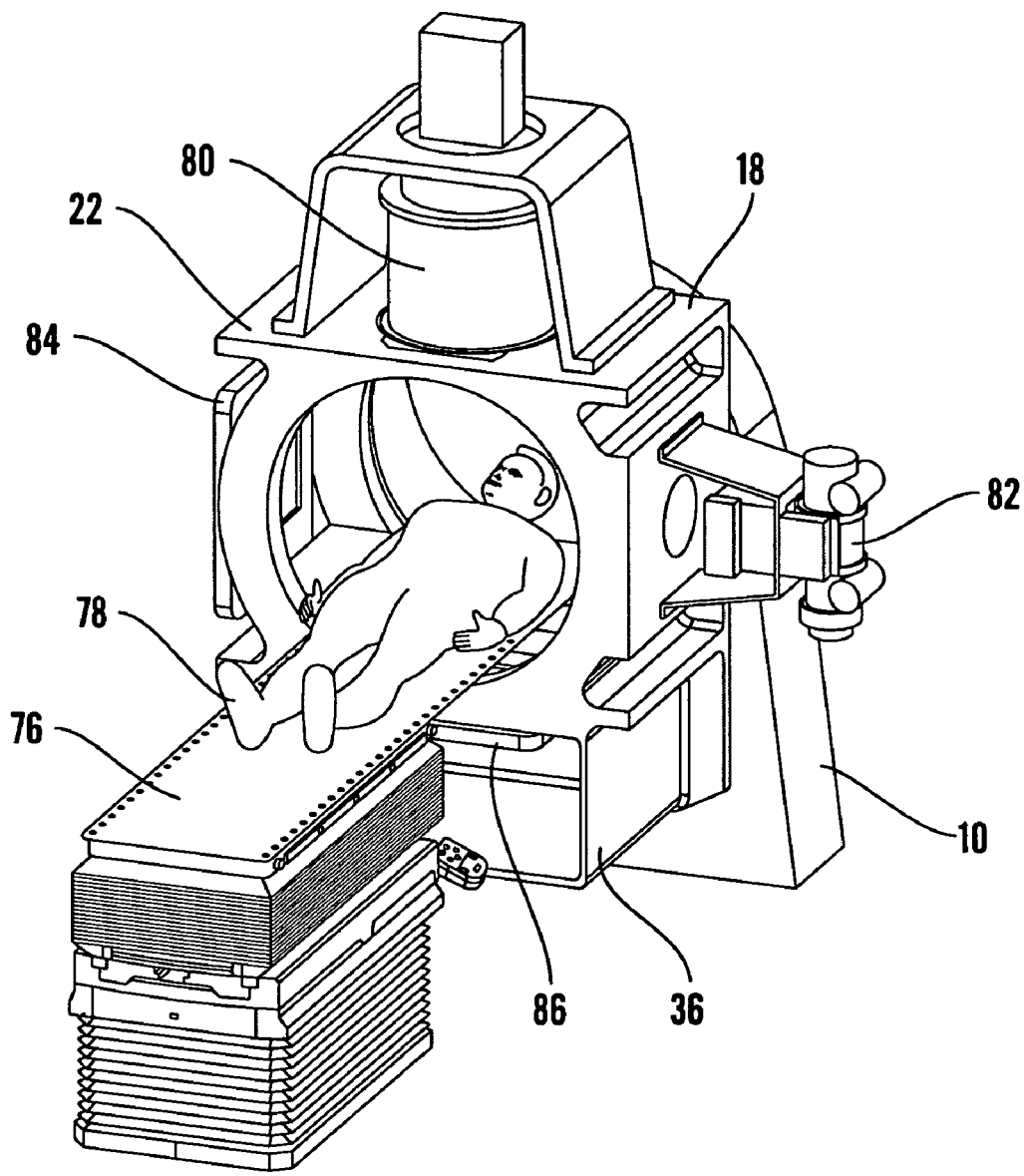
FIG. 11 shows a perspective view of the operative elements of a rotational therapy system based on the mount of the present invention.

FIG. 11 shows an alternative treatment arrangement. Again, the mount 18 is supported on a cylindrical bearing 16 which is supported on the base 10. In this case, however, a short therapeutic x-ray source 80 is disposed on the top base of the mount 18 so as to produce a beam passing through the top aperture 28 and into the through-hole of the mount body 22. A diagnostic x-ray source 82 is fixed to one side of the mount body 22 so as to project a beam of diagnostic x-rays through the central through-hole and to a flat panel detector 84 mounted to the other side of the mount body 22. A flat panel detector 86 for the therapeutic radiation is mounted within the box section 36. A beam stop (not shown) can be disposed in the remainder of the box section.

The patient table 76 is located so as to support a patient 78 within a central through-hole of the mount body 22, so that they are in the field of the short therapeutic source 80. The mount 18 can then rotate around the patient 78 so as to deliver radiation from a multiplicity of angles. Once this is done, diagnostic radiation from the source 82 is captured by the flat panel detector 84 after passing through the patient, therefore creating diagnostic images which can (as before) be assembled to form a computer tomography scan if desired. The short therapeutic source 80 can of course be collimated as desired, for example with a multi-leaf collimator.

Figure 12:
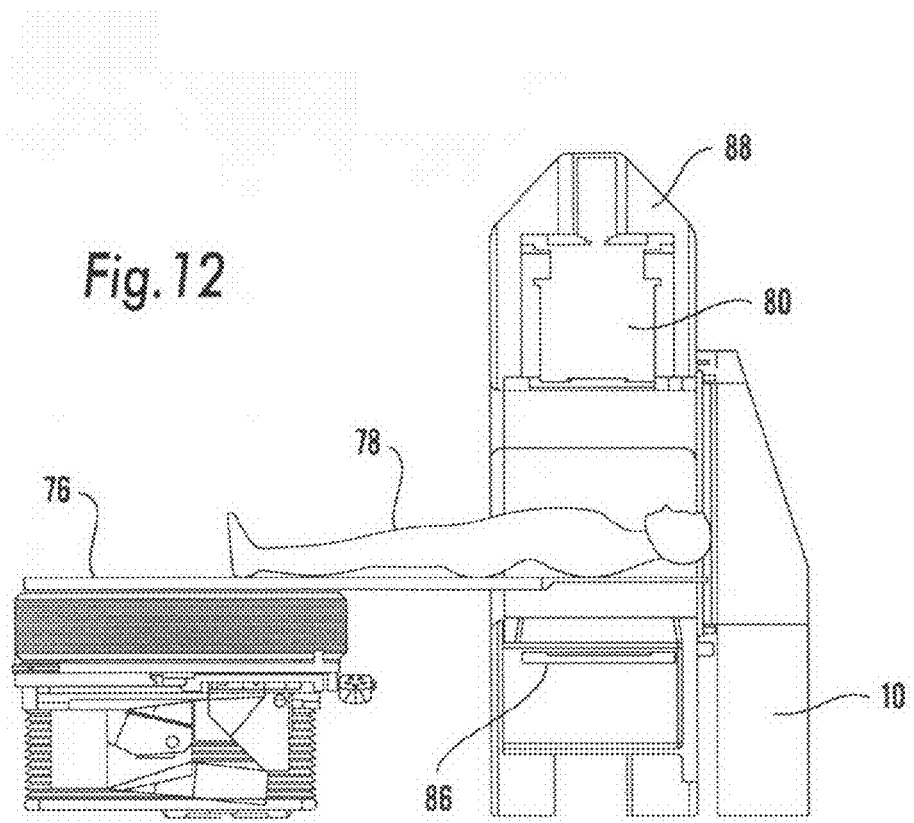
FIGS. 12 and 13 show the complete rotational therapy system treating a patient.
Figure 13:
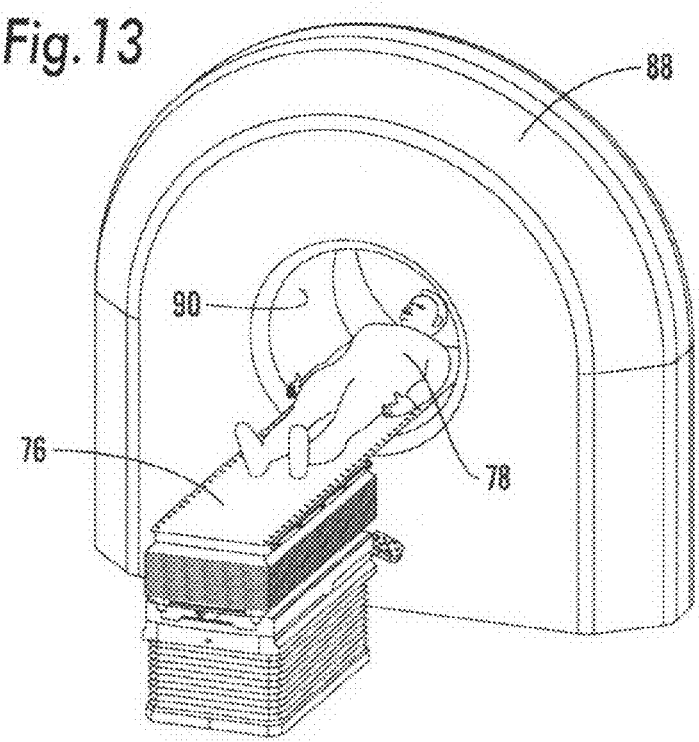

FIGS. 12 and 13 show an external casing 88 that can be applied to the device, to protect against accidents or injury as the mount 18 rotates. This extends in a toroidal manner around the device and has a tunnel 90 or other form of opening which extends within the through-hole of the mount body 22 to allow the patient 78 to project into the device. Radiation from the source 80 passes through the material of the cover 88 and is incident on a patient within the tunnel.

The rotating mount shown in FIG. 11 will usually enable continuous rotation by the use of a slip ring, as is known for Tomotherapy and other toroidally-configured apparatus that rely on continuous rotation. This allows the arrangement of FIG. 11 to mimic the operation of such devices notwithstanding the simpler manufacturing process that is required. It should be noted that the modular nature of the example disclosed herein permits the straightforward inclusion of a slip ring into either arrangement, thereby enabling the provision of a continuously rotatable C-arm linac.

Accordingly, the present invention provides an adaptable base unit to which can be attached various items of equipment as required to produce the desired radiotherapeutic apparatus.

It will of course be understood that many variations may be made to the above-described embodiment without departing from the scope of the present invention.

The invention claimed is:

1. A mount for a radiotherapy apparatus, comprising;
    a cylindrical bearing surface to allow the mount to be supported in a rotatable manner; and
    a housing extending from the bearing surface and having an extent in a direction along an axis of the cylindrical bearing surface,
    the mount configured to support the radiotherapy apparatus and having an axial through-hole which encompasses the axis of the cylindrical bearing surface,
    the housing having at least one opening communicating with the through-hole and extending in a direction transverse to the axis of the cylindrical bearing surface.

2. Radiotherapeutic apparatus, comprising;
    a support having a cylindrical bearing surface on which is mounted the cylindrical bearing surface of a mount according to claim 1,
    an arm extending from a side of the mount in a direction in line with the axis of the cylindrical bearing surface;
    the arm comprising a linear accelerator adapted to emit a beam of therapeutic radiation from an end portion of the arm in a direction transverse to and towards the axis of the cylindrical bearing surface.

3. Radiotherapeutic apparatus according to claim 2, further comprising a source of diagnostic radiation.

4. Radiotherapeutic apparatus according to claim 3, in which the source of diagnostic radiation is mounted on a retractable arm so as to be selectively retractable into the mount or extendable alongside the linear accelerator.

5. Radiotherapeutic apparatus according to claim 2, further comprising a detector for diagnostic radiation.

6. Radiotherapeutic apparatus according to claim 5, in which the detector for diagnostic radiation is mounted on a retractable arm so as to be selectively retractable into the mount or extendable alongside the linear accelerator.

7. Radiotherapeutic apparatus according to claim 2, further comprising a detector for therapeutic radiation.

8. Radiotherapeutic apparatus according to claim 7, in which the detector for therapeutic radiation is mounted on a retractable arm so as to be selectively retractable into the mount or extendable alongside the linear accelerator.

9. Radiotherapeutic apparatus according to claim 2 in which the therapeutic radiation has an energy of at least 1 MeV.

10. Radiotherapeutic apparatus according to claim 3 in which the diagnostic radiation has an energy of at least 1 keV.

11. Radiotherapeutic apparatus, comprising;
a support having a cylindrical bearing surface on which is mounted the cylindrical bearing surface of a mount according to claim 1,
a source of therapeutic radiation fixed to the mount and adapted to emit a beam transverse to and towards the axis of the cylindrical bearing surface though the at least one opening of the mount.

12. Radiotherapeutic apparatus according to claim 11, further comprising a source of diagnostic radiation.

13. Radiotherapeutic apparatus according to claim 11, further comprising a detector for diagnostic radiation.

14. Radiotherapeutic apparatus according to claim 11, further comprising a detector for therapeutic radiation.

15. Radiotherapeutic apparatus according to claim 11 in which a cover is provided around the mount, the cover including a concave region extending into the axial through-hole of the mount.

\* \* \* \* \*